United States Patent

Aprahamian

[11] 3,931,330
[45] Jan. 6, 1976

[54] PROCESS FOR THE PRODUCTION OF BENZALDEHYDE

[75] Inventor: Nazar S. Aprahamian, West Nyack, N.Y.

[73] Assignee: Union Carbide Corporation, New York, N.Y.

[22] Filed: May 4, 1972

[21] Appl. No.: 250,450

[52] U.S. Cl............................... 260/599; 260/600
[51] Int. Cl.²..............C07C 47/52; C07C 47/54; C07C 47/55
[58] Field of Search................ 260/599, 600, 618 C

[56] References Cited
UNITED STATES PATENTS
2,673,217  3/1954  Hull .......................... 260/618 C X FOREIGN PATENTS OR APPLICATIONS
119,517  10/1918  United Kingdom................. 260/599

OTHER PUBLICATIONS
Yamashita et al., "Chem. Soc. of Japan," Journal, Industrial Chemical Section Abstract, p. A68, Vol. 67, Nov. 1964.
Marimoto et al., J. Chem. Soc.(B), 1967, pp. 1353–1356.

Primary Examiner—Donald G. Daus
Assistant Examiner—D. B. Springer
Attorney, Agent, or Firm—Bernard Lieberman

[57] ABSTRACT

A liquid phase co-oxidation process for the production of a benzaldehyde compound having the following structural formula:

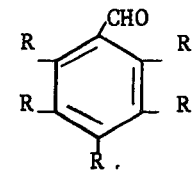

wherein R is selected from the group of radicals consisting of hydrogen, halogen, methyl, and methoxy comprising admixing a toluene compound having the following structural formula:

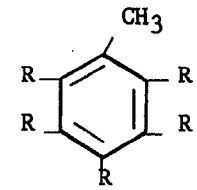

wherein R is as defined above with an aliphatic saturated aldehyde consisting of carbon, hydrogen, and oxygen atoms and having 2 to 7 carbon atoms and an oxygen containing gas wherein the molar ratio of toluene compound to aldehyde is preferably about 1 to about 25 mols of toluene compound per mol of aldehyde and the temperature is in the range of about 50° to about 250°C.

11 Claims, No Drawings

PROCESS FOR THE PRODUCTION OF BENZALDEHYDE

FIELD OF THE INVENTION

This invention relates to a process for the production of benzaldehyde and derivatives thereof and, more particularly, to a liquid phase process for the production of such benzaldehydes by the indirect oxidation of toluene or various substituted toluenes.

DESCRIPTION OF THE PRIOR ART

Benzaldehyde and its derivatives are well known in the chemical industry, many being in the category of expensive chemicals. Benzaldehyde, particularly, is useful in organic synthesis especially of dyes and intermediates; as a solvent for various oils, resins, and cellulose ethers, and for cellulose acetate and nitrate; in flavoring compounds, perfumes, and soaps; in photographic and baking chemicals; and in medicine. Several of the substituted benzaldehydes have similar utility especially in dye synthesis, e.g., 2,6-dichlorobenzaldehyde.

Many processes for the preparation of benzaldehyde have been proposed over the years, the most important of which utilize toluene as a starting material. One method follows the procedure of sidechain chlorination, fractionation, and hydrolysis of the benzal chloride formed thereby; another method involves the partial oxidation of toluene with manganese dioxide in a sulfuric acid solution followed by steam distillation; and one more involves the vapor-phase air oxidation of toluene in the presence of a vanadium pentoxide catalyst. These and other prior art processes have, unfortunately, been marked by one or more of the following disadvantages: low efficiencies, low conversions, poor selectivity, slow reaction rates, impurities or instability in the final product, commercially unattractive by-products, or the need, in some cases, for expensive initial reactants.

SUMMARY OF THE INVENTION

An object of the invention, therefore, is to provide a highly selective process for the production of benzaldehyde and various of its derivatives from the corresponding toluene compound, which raises efficiencies and conversions, increases reaction rates, reduces impurity levels, provides stable products, and uses inexpensive initial reactants.

Other objects and advantages will become apparent hereinafter.

According to the present invention, a highly selective liquid phase co-oxidation process for the production of a benzaldehyde compound having the following structural formula:

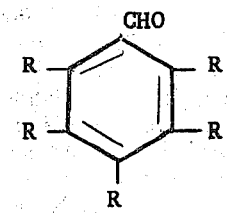

wherein R is selected from the group of radicals consisting of hydrogen, halogen, methyl, and methoxy has been discovered, which effectively overcomes the aforementioned disadvantages, comprising admixing a toluene compound having the following structural formula:

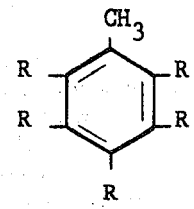

wherein R is as defined above with an aliphatic saturated aldehyde consisting of carbon, hydrogen, and oxygen atoms and having 2 to 7 carbon atoms and an oxygen containing gas wherein the molar ratio of toluene compound to aldehyde is about 0.1 to about 250 mols of toluene compound per mol of aldehyde and the temperature is in the range of about 50° to about 250°C.

DESCRIPTION OF THE PREFERRED EMBODIMENT

The process can be carried out be feeding a mixture of toluene or its derivative and an aldehyde into a reaction vessel. The reaction vessel can be glass, glass-lined or made of aluminum or titanium. A glass-lined polytetrafluoroethylene coated stainless steel autoclave can be used or even better from a commercial point of view, it is found that unlined type 316 stainless steel (as defined by the American Iron and Steel Institute) can be used effectively. A tubular or backmixed reactor made of similar materials can also be used together with multipoint injection to maintain a particular ratio of reactants.

Some form of agitation is preferred to avoid a static system and can be accomplished by using a mechanically stirred autoclave, a multipoint injection system, or a loop reactor wherein the reactants are force circulated through the system. Sparging can also be used. In subject process, it is found that increased rates of reaction are obtained by good gas-liquid contact throughout and that this contact is provided by agitation. The homogeneity of the liquid reactants, provided by the agitation, is also advantageous. In this regard, the type of reactor which is most preferred herein is a back mixed reactor since it is effective in maintaining optimum steady state reactio of reactants in a continuous operation.

Toluene and the derivatives which are useful in this process can be defined by the following structural formula:

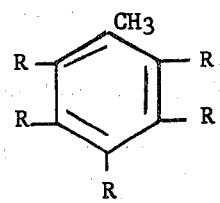

wherein R can be selected from the group of radicals consisting of hydrogen, halogen (chlorine, bromine, iodine, and fluorine), methyl, and methoxy. Examples of these compounds, in addition to toluene, are ortho-, meta-, and para-xylene, ortho-, meta-, and para-chlorotoluene, 2,6-dichlorotoluene, paramethoxytoluene, and ortho-bromotoluene. For the sake of brevity, this group of compounds may hereinafter be referred to as the "toluene compound."

The aldehyde is preferably acetaldehyde but can be any aliphatic saturated aldehyde which contains only carbon, hydrogen, and oxygen. It can be straight chain or branched and can have from two to seven carbon atoms. Examples of saturated aldehydes of this type are propionaldehyde, n-butyraldehyde, isobutyraldehyde, n-valeraldehyde, isovaleraldehyde, n-caproaldehyde, n-heptaldehyde, and trimethylacetaldehyde.

The molar ratio of toluene compound to aldehyde introduced into the reaction mixture is critical and must be in the range of about 0.1 mol to about 250 mols of toluene compound to one mol of aldehyde. The preferred range is about 1 mol to about 25 mols of toluene compound per mol of aldehyde.

The reaction can be carried out at temperatures ranging from about 50°C. to about 250°C. The preferred temperature range is about 80°C. to about 180°C. The temperature is also critical.

The pressure under which the reaction vessel is maintained, however, is not critical and there is no upper limit except the practical limitation in cost and size of the reactor. Pressures of atmospheric to about 100 atmospheres are adequate to maintain a substantial portion of the toluene compound in the liquid phase depending on the temperature at which the reaction is run and the boiling point of the particular toluene compound. Pressures between about 10 atmospheres and about 30 atmospheres are generally used, however.

The temperature, pressure, and feed determine how much of the toluene compound is in the liquid phase, which is only important in the following respect since excess toluene compound can easily be recycled. There is nothing objectionable about the presence of a vapor phase, but it should be noted that to achieve the desired results the prescribed ratios have to be correct in the liquid phase where the reaction is taking place.

The atmosphere in the reaction vessel prior to the introduction of oxygen can be comprised of nitrogen or other inert gas, if desired.

An oxygen containing gas wherein the balance of the components of the gas are inert to the reaction such as a mixture of nitrogen and oxygen, air, or oxygen itself is then introduced into the reaction vessel. Generally, the oxygen is introduced under partial pressures such as about 50 to 350 psi. The pressure is not critical. Pressure loss due to consumption of oxygen is adjusted to a constant pressure by the addition of more oxygen. The amount of oxygen used can be based on the aldehyde with which it directly reacts. Advantageous molar ratios of $O_2$ to aldehyde are about 1:1 or less and preferably about 1:2 or less with an optimum of about 1:4. A molar ratio of 1:20 or less is unproductive, however, and a molar excess of $O_2$, while operative, is a waste of oxygen, reduces efficiency and is hazardous. In terms of oxygen partial pressures, very low pressures can be used and the better the method of oxygen transfer, the lower the partial pressure. Agitation is the key to good oxygen transfer and can be provided as mentioned above. High partial pressures can also be used, if desired.

This process can be run in a batchwise, semi-continuous or continuous operation, the latter being preferred. The order of introduction of the reactants is determined by the operator based on what is most practical under prevalent conditions and is not of a critical nature.

Catalysts and initiators are not necessary to the reaction, but can be present. A particular and preferred feature of this invention involves the use of a catalyst and will be described below.

The benzaldehyde product which is formed has the following structural formula:

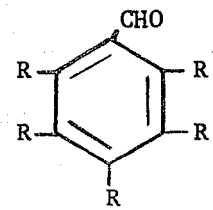

wherein R is the same as defined above for the toluene compound. This product may be referred to herein as the "benzaldehyde compound."

A feature of this invention is the formation of a benzyl alcohol by-product. Benzyl alcohol is an extremely valuable industrial product and although it is not formed in as high a proportion as benzaldehyde, its formation is, nevertheless, so desirable that selectivities in the examples are based on the combined selectivity to benzaldehyde and benzyl alcohol.

Another by-product of subject process is the carboxylic acid which corresponds to the aldehyde reactant, e.g., where acetaldehyde is reacted, acetic acid is formed and where butyraldehyde is reacted, butyric acid is formed. It will be noted that this by-product is formed in larger molar quantities than the desired products. Since these carboxylic acids are useful, their formation is not detrimental to the process. From a commercial point of view, however, they are not nearly as valuable as, e.g, benzaldehyde and benzyl alcohol. Therefore, optimization of subject process also entails, e.g., low acetic acid: benzaldehyde-benzyl alcohol molar ratios.

Other by-products formed in small quantities and, in some cases, not at all are methanol or the corresponding alkanols and benzoic acid or its corresponding derivatives. Water is also generally formed in minor amounts.

As noted above, a feature of this invention involves the use of a catalyst. In the course of experimentation, it was found that all of the above-mentioned disadvantages of the prior art processes could be substantially overcome by the process described heretofore except for that of low conversion of toluene. While some improvement in the conversion of toluene was achieved, any attempt at substantial improvement by varying process conditions was met with a corresponding decrease in selectivity. A careful study of this phenomenon led to the discovery that the source of the problem was the presence of a small quantity (no more than about 500 parts per million based on the weight of the toluene compound) of a phenol, which evidently is formed during the process. Phenol and related compounds are, of course, known oxidation inhibitors. In fact, benzaldehyde is often treated with hydroquinone to prevent its autoxidation to benzoic acid while in storage. It was then found that the solution to the problem of low conversion was accomplished by introducing small amounts of transition metal catalysts into the reaction mixture. The minimum amount of catalyst that can be used is about 10 parts by weight of catalyst per million parts by weight of toluene compound. There is no upper limit except the limit of practicality in view of the high cost of the catalyst. The amount of catalyst used is preferably in the range of about 20 to about 100 parts by weight per million parts by weight of toluene compound. The catalyst can be any one of the transition metals selected from Groups I B to VII B, inclusive, and VIII of the Periodic Table in a free state, or in compound or complex form. The compound or complex can be inorganic or organic, the latter being preferred.

Preferred metals are cobalt, manganese, and chromium.

Examples of useful catalysts which are inorganic compounds or complexes are: cobalt chloride, cobalt sulfate, manganese chloride, manganese sulfate, chromium chloride, chromium sulfate, and iron chloride.

Examples of useful catalysts which are organic compounds or complexes are: cobalt naphthenate, cobalt (II) acetylacetonate, cobalt acetate, manganese (II) acetylacetonate, manganese naphthenate, and manganese acetate.

It is found that the use of these catalysts in the process overcomes the inhibition of reaction rates by phenols and a marked increase in the conversion of toluene is achieved thereby.

Recovery, separation and analysis of products and unreacted materials are accomplished by conventional means.

The percent selectivity to benzaldehyde and benzyl alcohol is calculated as follows:

$$\frac{\text{no. of mols of benzaldehyde compound} + \text{no. of mols of benzyl alcohol compound}}{\text{no. of mols of toluene compound reacted}}$$

The following examples illustrate the invention. Parts are by weight.

Note: In the examples dealing with acetaldehyde, chlorobenzene is used as an internal standard, and in examples dealing with butyraldehyde, 1,2,4-trichlorobenzene is used as an internal standard. Internal standards are commonly used in laboratory experiments where analysis is to be accomplished by gas phase chromotography as is the case in the following examples. By definition these internal standards must be non-reactive and non-volatile so as not to interfere with the results of the experiment. Any organic chemical which meets the definition can be used. The internal standards serve as a gauge for measuring quantities of components, reactants or products.

EXAMPLES 1 to 19

These examples are a series of batch reactions. The reactants, i.e., toluene and aldehyde, are introduced into a glass-lined stainless steel autoclave (examples 1 to 16) or an all glass reactor (examples 17 to 19). Oxygen and nitrogen or just oxygen are fed into the reactor. Reactants, conditions and results are set forth in Table I.

Table I

| Example | Name of aldehyde | Temp. (°C) | Toluene (mols) | Aldehyde (mols) | Toluene (parts by weight) | Aldehyde (parts by weight) | Oxygen (psi) | Nitrogen (psi) | Reaction time (minutes) |
|---|---|---|---|---|---|---|---|---|---|
| 1 | acetaldehyde | 100 | 2.175 | 0.5 | 200 | 22 | 50 | 350 | 5 |
| 2 | acetaldehyde | 100 | 2.175 | 0.5 | 200 | 22 | 50 | 350 | 30 |
| 3 | acetaldehyde | 100 | 2.175 | 0.5 | 200 | 22 | 50 | 350 | 330 |
| 4 | acetaldehyde | 100 | 2.175 | 0.1 | 200 | 4.4 | 50 | 350 | 30 |
| 5 | acetaldehyde | 100 | 2.175 | 0.1 | 200 | 4.4 | 50 | 350 | 40 |
| 6 | acetaldehyde | 120 | 2.175 | 0.1 | 200 | 4.4 | 50 | 350 | 10 |
| 7 | acetaldehyde | 120 | 2.175 | 0.1 | 200 | 4.4 | 50 | 350 | 20 |
| 8 | acetaldehyde | 120 | 2.175 | 0.1 | 200 | 4.4 | 50 | 350 | 30 |
| 9 | acetaldehyde | 120 | 2.175 | 0.1 | 200 | 4.4 | 50 | 350 | 40 |
| 10 | acetaldehyde | 140 | 2.175 | 0.1 | 200 | 4.4 | 50 | 350 | 5 |
| 11 | acetaldehyde | 140 | 2.175 | 0.1 | 200 | 4.4 | 50 | 350 | 10 |
| 12 | acetaldehyde | 160 | 2.175 | 0.1 | 200 | 4.4 | 50 | 350 | 5 |
| 13 | acetaldehyde | 160 | 2.175 | 0.1 | 200 | 4.4 | 50 | 350 | 10 |
| 14 | acetaldehyde | 160 | 2.175 | 0.1 | 200 | 4.4 | 50 | 350 | 20 |
| 15 | acetaldehyde | 160 | 2.175 | 0.1 | 200 | 4.4 | 50 | 350 | 30 |
| 16 | acetaldehyde | 160 | 2.175 | 0.1 | 200 | 4.4 | 50 | 350 | 40 |
| 17 | butyraldehyde | 100 | 1.0 | 0.1 | 92 | 7.2 | 14.3 | — | 45 |
| 18 | butraldehyde | 100 | 1.0 | 0.1 | 92 | 7.2 | 14.3 | — | 240 |
| 19 | butraldehyde | 100 | 1.0 | 0.1 | 92 | 7.2 | 14.3 | — | 320 |

| Example | benzaldehyde (mols) | Products Benzyl alcohol (mols) | Benzoic acid (mols) | Selectivity to benzaldehyde + benzyl alcohol (mol percent) |
|---|---|---|---|---|
| 1 | 0.022 | 0.004 | 0.003 | 87.9 |
| 2 | 0.030 | 0.004 | 0.012 | 73.3 |
| 3 | 0.030 | 0.003 | 0.012 | 72.5 |
| 4 | 0.005 | 0 | 0 | 100 |
| 5 | 0.007 | 0 | 0 | 100 |
| 6 | 0.012 | 0 | 0 | 100 |
| 7 | 0.014 | trace | 0.001 | 94 |
| 8 | 0.015 | trace | 0.001 | 94 |
| 9 | 0.015 | trace | 0.001 | 94 |
| 10 | 0.012 | 0.002 | 0 | 100 |
| 11 | 0.013 | 0.002 | 0.001 | 97 |
| 12 | 0.015 | 0.005 | 0.001 | 96 |
| 13 | 0.016 | 0.008 | 0.001 | 96 |
| 14 | 0.015 | 0.008 | 0.002 | 92 |
| 15 | 0.019 | 0.009 | 0.004 | 86 |
| 16 | 0.019 | 0.008 | 0.004 | 86 |
| 17 | 0.002 | 0.001 | 0 | 100 |
| 18 | 0.004 | 0.001 | 0 | 100 |
| 19 | 0.004 | 0.001 | 0 | 100 |

EXAMPLE 20

This example demonstrates a semicontinuous reaction in all glass reactor. All conditions are kept constant except for the butyraldehyde feed.

92 parts by weight of toluene (1mol) are introduced into the all glass reactor. The temperature is maintained at 100°C. Sufficient oxygen is introduced and added during the course of the reaction to maintain an oxygen pressure of 14.3 psi in the reactor. 38.8 parts by weight of butyraldehyde (0.54 mol) are added to the reactor, 10 parts initially and the balance is pumped in, in roughly about equal portions by volume, every half hour over 614 minutes during the run.

The results are in millimols, except as otherwise specified, as follows:

| reaction time (minutes) | 87 | 159 | 221 | 296 | 614 |
|---|---|---|---|---|---|
| benzaldehyde | 3.0 | 4.0 | 4.4 | 5.8 | 9.7 |
| benzyl alcohol | 1.2 | 1.9 | 1.9 | 1.7 | 4.0 |
| benzoic acid | 0.0 | 0.0 | 0.0 | 0.2 | 3.7 |
| selectivity to benzaldehyde + benzyl alcohol (mol percent) | 100 | 100 | 100 | 97 | 79 |
| toluene conversion (weight percent) | .44 | .62 | .65 | .80 | 1.9 |

EXAMPLE 21

This example demonstrates a semi-continuous reaction in a glass-lined stainless steel reactor. All conditions are kept constant except for the butyraldehyde feed.

200 parts by weight of toluene (2.18 mols) are introduced into the reactor. The temperature is maintained at 100°C. Sufficient oxygen is introduced and added during the course of the reaction to maintain an oxygen partial pressure of 50 psi. Sufficient nitrogen is introduced and added during the course of the reaction to maintain a nitrogen partial pressure of 150 psi. 2 parts by weight of butyraldehyde are introduced into the reactor initially. 24.5 parts by weight of butyraldehyde are fed by pump in about equal portions by volume each minute thereafter for twenty minutes (total aldehyde: 0.37 mol).

The results are in millimols, except as otherwise specified, as follows:

| reaction time (minutes) | 5 | 10 | 15 | 20 |
|---|---|---|---|---|
| benzaldehyde | 15.1 | 15.1 | 20.0 | 20.3 |
| benzyl alcohol | 5.3 | 6.2 | 4.8 | 4.8 |
| benzoic acid | 4.4 | 6.9 | 11.0 | 17.2 |
| selectivity to benzaldehyde + benzyl alcohol (mol percent) | 83 | 76 | 69 | 59 |
| toluene conversion (weight percent) | 1.2 | 1.3 | 1.7 | 2.0 |

EXAMPLE 22

Example 21 is repeated except that 4 parts by weight of butyraldehyde are introduced initially and an additional 81.7 parts by weight are introduced in about equal portions by volume each minute for 50 minutes (total aldehyde: 1.19 mol).

The results are in millimols, except as otherwise specified, as follows:

| reaction time (minutes) | 10 | 15 | 20 | 30 | 50 |
|---|---|---|---|---|---|
| benzaldehyde | 21.0 | 25.3 | 25.2 | 31.0 | 27.5 |
| benzyl alcohol | 4.3 | 3.3 | 4.2 | 5.4 | 8.9 |
| benzoic acid | 8.8 | 10.2 | 18.7 | 24.0 | 31.0 |
| selectivity to benzaldehyde + benzyl alcohol (mol percent) | 74 | 74 | 61 | 61 | 54 |
| toluene conversion (weight percent) | 1.6 | 1.8 | 2.3 | 2.9 | 3.2 |

EXAMPLE 23

Example 22 is repeated except that the additional parts by weight of butyraldehyde are changed to 49 parts by weight, which are introduced in about equal portions by volume each minute for 30 minutes, and the oxygen partial pressure is changed to 350 psi and the nitrogen partial pressure is changed to 50 psi (total aldehyde: 0.74 mol).

The results are in millimols, except as otherwise specified, as follows:

| reaction time (minutes) | 5 | 10 | 15 | 20 | 30 |
|---|---|---|---|---|---|
| benzaldehyde | 14.5 | 22.1 | 25.7 | 31.5 | 28.4 |
| benzyl alcohol | 1.9 | 1.3 | 2.6 | 3.6 | 5.9 |
| benzoic acid | 2.0 | 12.3 | 19.8 | 30.4 | 55.8 |
| selectivity to benzaldehyde + benzyl alcohol (mol percent) | 88 | 65 | 59 | 54 | 38 |
| toluene conversion (weight percent) | 0.9 | 1.7 | 2.3 | 3.1 | 4.3 |

EXAMPLE 24

Example 23 is repeated except that the temperature is raised to 120°C.; the additional parts by weight of butyraldehyde are changed to 73.5 parts by weight, which are introduced in about equal portions by volume each minute for 45 minutes; and the oxygen partial pressure is 150 psi and, after 30 minutes, is increased to 240 psi (total aldehyde: 1.08 mol)

Results in millimols, except as otherwise specified, are as follows:

| reaction time (minutes) | 10 | 15 | 20 | 30 | 45 |
|---|---|---|---|---|---|
| benzaldehyde | 21.3 | 21.4 | 21.0 | 19.5 | 29.7 |
| benzyl alcohol | 11.5 | 10.9 | 8.8 | 10.5 | 17.7 |
| benzoic acid | 14.3 | 8.2 | 11.0 | 13.1 | 31.8 |
| selectivity to benzaldehyde + benzyl alcohol (mol percent) | 70 | 80 | 73 | 70 | 60 |
| toluene conversion (weight percent) | 2.3 | 1.9 | 1.9 | 2.0 | 3.7 |

EXAMPLE 25

Example 23 is repeated except that the temperature is raised to 140°C.

Results in millimols, except as otherwise specified, as follows:

| reaction time (minutes) | 5 | 10 | 15 | 20 | 30 |
|---|---|---|---|---|---|
| benzaldehyde | 20.7 | 28.0 | 30.6 | 32.0 | 38.9 |
| benzyl alcohol | 3.1 | 3.5 | 3.8 | 8.4 | 12.8 |
| benzoic acid | 6.9 | 15.6 | 17.9 | 38.9 | 74.7 |
| selectivity to benzaldehyde + benzyl alcohol: (mol percent) | 78 | 67 | 66 | 51 | 41 |
| toluene conversion (weight percent) | 1.5 | 2.2 | 2.5 | 3.8 | 6.0 |

EXAMPLE 26

Example 22 is repeated except that 2.5 parts by weight of butyraldehyde are introduced initially and an additional 24.5 parts by weight are introduced in about equal portions by volume each minute for sixty minutes (total aldehyde: 0.38 mol).

Results in millimols, except as otherwise specified as follows:

| reaction time (minutes) | 30 | 45 | 60 |
|---|---|---|---|
| benzaldehyde | 21.1 | 26.4 | 28.4 |
| benzyl alcohol | 7.3 | 8.6 | 11.5 |
| benzoic acid | 85.1 | 87.6 | 113.8 |
| selectivity to benzaldehyde + benzyl alcohol (mol percent) | 25 | 28.5 | 26 |
| toluene conversion (weight percent) | 5.3 | 5.8 | 7.3 |

EXAMPLE 27

Example 22 is repeated except that the additional amount of butyraldehyde is 147 parts by weight introduced in about equal portions by volume each minute for 90 minutes; and the temperature is changed to 70°C. (total aldehyde: 2.10 mols).

Results are set forth in millimols, except as otherwise specified, as follows:

| reaction time (minutes) | 10 | 60 | 90 |
|---|---|---|---|
| benzaldehyde | 3.40 | 22.2 | 26.9 |
| benzyl alcohol | 0.40 | 4.3 | 4.9 |
| benzoic acid | 0.0 | 20.9 | 18.1 |
| selectivity to benzaldehyde + benzyl alcohol (mol percent) | 100 | 56 | 64 |
| toluene conversion (weight percent) | 0.2 | 2.3 | 2.3 |

EXAMPLE 28

Example 26 is repeated except that 2 parts by weight of butyraldehyde are introduced initially and an additional 25.5 parts by weight are introduced in about equal portions by volume each minute for 12 minutes; and 0.004 part by weight of cobalt (II) acetylacetonate is introduced initially into the reaction mixture (total aldehyde: 0.38 mol).

Results are in millimols, except as otherwise specified, as follows:

| reaction time (minutes) | 3 | 6 | 9 | 12 |
|---|---|---|---|---|
| benzaldehyde | 12.2 | 18.0 | 21.9 | 26.2 |
| benzyl alcohol | 4.11 | 5.7 | 6.1 | 7.3 |
| benzoic acid | 0.4 | 7.1 | 12.4 | 23.3 |
| toluene conversion (weight percent) | 0.8 | 1.4 | 1.9 | 2.6 |
| selectivity to benzaldehyde + benzyl alcohol (mol percent) | 96.9 | 76.9 | 69.3 | 60.0 |

EXAMPLE 29

Example 28 is repeated except that the temperature is changed to 120°C.; the additional butyraldehyde is in an amount of 49 parts by weight introduced in about equal portions by volume each minute for 30 minutes; and the partial pressure of nitrogen is 300 psi and that of oxygen is 100 psi. (total aldehyde: 0.71 mol)

Results are set forth in millimols, except as otherwise specified, as follows:

| reaction time (minutes) | 6 | 9 | 12 | 30 |
|---|---|---|---|---|
| benzaldehyde | 16.2 | 25.9 | 30.3 | 34.8 |
| benzyl alcohol | 7.0 | 8.7 | 10.6 | 16.3 |
| benzoic acid | 3.7 | 21.2 | 34.8 | 59.3 |
| toluene conversion (weight percent) | 1.2 | 2.6 | 3.5 | 5.1 |
| selectivity to benzaldehyde + benzyl alcohol (mol percent) | 86.2 | 62.0 | 54.0 | 46.3 |

EXAMPLE 30

Example 29 is repeated except that the initial amount of butyraldehyde is 4 parts by weight and the additional butyraldehyde is introduced in an amount of 73.5 parts by weight in equal portions by volume each minute for 45 minutes; the partial pressure of nitrogen is 150 psi and the partial pressure of oxygen is 50 psi; and the amount of cobalt (II) acetylacetonate is 0.002 part by weight (total aldehyde: 1.08 mol).

Results are in millimols, except as otherwise specified, as follows:

| reaction time (minutes) | 10 | 20 | 30 | 45 |
|---|---|---|---|---|
| benzaldehyde | 26.1 | 26.9 | 30.1 | 27.7 |
| benzyl alcohol | 8.4 | 13.0 | 16.2 | 18.1 |
| benzoic acid | 38.7 | 67.4 | 71.3 | 75.2 |
| toluene conversion (weight percent) | 3.4 | 4.9 | 5.4 | 5.6 |
| selectivity to benzaldehyde + benzyl alcohol (mol percent) | 47 | 37.2 | 39.3 | 37.9 |

EXAMPLE 31

Example 28 is repeated except that the temperature is changed to 140°C.; the initial amount of butyraldehyde is 6 parts by weight and an additional 53 parts by weight are intorduced in about equal portions by volume each minute for 25 minutes; and the partial pressure of nitrogen is 300 psi and that of oxygen is 100 psi (total aldehyde: 0.82 mol).

Results are in millimols, except as otherwise specified, as follows:

| reaction time (minutes) | 3 | 6 | 9 | 12 | 25 |
|---|---|---|---|---|---|
| benzaldehyde | 19.1 | 33.6 | 42.1 | 49.9 | 48.8 |
| benzyl alcohol | 7.9 | 13.4 | 16.6 | 13.1 | 14.5 |
| benzoic acid | 4.3 | 27.1 | 61.9 | 92.7 | 142.5 |
| toluene conversion (weight percent) | 1.4 | 3.4 | 5.5 | 7.2 | 9.5 |
| selectivity to benzaldehyde + benzyl alcohol (mol percent) | 86.3 | 63.4 | 48.6 | 40.5 | 30.8 |

EXAMPLE 32

Example 31 is repeated except that the temperature is changed to 160°C.; and the initial amount of butyraldehyde is 12 parts by weight and an additional 68 parts by weight are introduced in about equal portions by volume each minute for 32 minutes (total aldehyde: 1.11 mol).

Results are in millimols, except as otherwise specified, as follows:

| reaction time (minutes) | 3 | 9 | 12 | 22 | 32 |
|---|---|---|---|---|---|
| benzaldehyde | 23.7 | 36.5 | 41.6 | 44.2 | 44.9 |
| benzyl alcohol | 13.9 | 25.7 | 19.8 | 26.3 | 17.8 |
| benzoic acid | 20.4 | 75.4 | 91.9 | 117.5 | 149.2 |
| toluene conversion (weight percent) | 2.7 | 6.3 | 7.1 | 8.6 | 9.7 |
| selectivity to benzaldehyde + benzyl alcohol (mol percent) | 64.8 | 45.2 | 40.1 | 37.5 | 29.6 |

EXAMPLE 33

Example 32 is repeated except that the initial amount of butyraldehyde is 24 parts by weight and an additional 42.5 parts by weight are introduced in about equal portions by volume each minute for twenty minutes; and the partial pressures of both nitrogen and oxygen are 200 psi (total aldehyde: 0.92 mol).

Results are in millimols, except as otherwise specified, as follows:

| reaction time (minutes) | 2 | 4 | 6 | 8 | 10 | 20 |
|---|---|---|---|---|---|---|
| benzaldehyde | 32.5 | 47.1 | 53.6 | 52.9 | 58.9 | 59.6 |
| benzyl alcohol | 27.3 | 26.7 | 25.6 | 29.9 | 29.7 | 37.7 |
| benzoic acid | 25.6 | 34.9 | 61.8 | 79.7 | 88.1 | 163.7 |
| toluene conversion (weight percent) | 3.9 | 5.0 | 6.5 | 7.5 | 8.1 | 12.0 |
| selectivity to benzaldehyde + benzyl alcohol (mol percent) | 70.0 | 68.0 | 56.2 | 51.0 | 50.1 | 37.3 |

EXAMPLE 34

Example 33 is repeated except that the initial amount of butyraldehyde is 30 parts by weight (total aldehyde: 1.01 mol).

Results are in millimols, except as otherwise specified, as follows:

| reaction time (minutes) | 2 | 4 | 6 | 8 | 10 | 20 |
|---|---|---|---|---|---|---|
| benzaldehyde | 36.2 | 41.2 | 47.2 | 46.9 | 45.6 | 64.0 |
| benzyl alcohol | 29.9 | 30.2 | 30.9 | 28.3 | 29.8 | 34.5 |
| benzoic acid | 16.5 | 31.3 | 48.0 | 71.1 | 83.9 | 130.6 |
| toluene conversion (weight percent) | 3.8 | 4.7 | 5.8 | 6.7 | 7.3 | 10.5 |
| selectivity to benzaldehyde + benzyl alcohol (mol percent) | 80.0 | 69.5 | 61.9 | 51.4 | 47.3 | 43 |

The Periodic Table referred to above appears in the Handbook of Chemistry and Physics, 46th edition, published by the Chemical Rubber Co. (1965–66) inside back cover.

I claim:

1. A liquid phase process for the production of benzaldehyde consisting essentially of admixing in the presence of a chromium, cobalt, iron or manganese containing catalyst, toluene with an aliphatic saturated aldehyde consisting of carbon, hydrogen, and oxygen atoms and having 2 to 7 carbon atoms and a molecular oxygen containing gas wherein the molar ratio of toluene to aldehyde is about 0.1 to about 250 mols of toluene per mol of aldehyde, the molar ratio of oxygen to aldehyde is about 1:1 to greater than 1:20, and the temperature is in the range of about 50°C to about 250°C.

2. The process defined in claim 1 wherein the molar ratio of toluene to aldehyde is about 1 to about 25 mols of toluene per mol of aldehyde and the molar ratio of oxygen to aldehyde is about 1:1 to about 1:4.

3. The process defined in claim 2 wherein the temperature is in the range of about 80° to about 180°C.

4. The process defined in claim 3 wherein the aldehyde is acetaldehyde or butyraldehyde.

5. The process defined in claim 1 wherein the said catalyst is introduced into the admixture in an amount in the range of about 20 to about 100 parts by weight per million parts by weight of toluene.

6. The process defined in claim 5 wherein the said catalyst is selected from the group consisting of free metals, inorganic compounds or complexes, and organometallic compounds or complexes.

7. The process defined in claim 6 wherein the molar ratio of toluene to aldehyde is about 1 to about 25 mols of toluene per mol of aldehyde and the molar ratio of oxygen to aldehyde is about 1:1 to about 1:4.

8. The process defined in claim 7 wherein the temperature is in the range of about 80° to about 180°C.

9. The process defined in claim 8 wherein the aldehyde is acetaldehyde or butyraldehyde.

10. The process defined in claim 8 wherein the catalyst is an organo-metallic compound having a metallic moiety of chromium, cobalt, iron or manganese.

11. The process defined in claim 10 wherein the organic moiety is acetylacetonate or napthenate.

* * * * *